(12) United States Patent
Hsieh et al.

(10) Patent No.: US 7,851,593 B2
(45) Date of Patent: Dec. 14, 2010

(54) BINDING PROTEINS AS BIOSENSORS

(75) Inventors: Helen Vivian Hsieh, Durham, NC (US); J. Bruce Pitner, Durham, NC (US); Terry J. Amiss, Cary, NC (US); Colleen M. Nycz, Raleigh, NC (US); Douglas B. Sherman, Durham, NC (US); David J. Wright, Madison, WI (US)

(73) Assignee: Becton, Dickinson and Company, Franklin Lakes, NJ (US)

( * ) Notice: Subject to any disclaimer, the term of this patent is extended or adjusted under 35 U.S.C. 154(b) by 1901 days.

(21) Appl. No.: 10/776,643

(22) Filed: Feb. 12, 2004

(65) Prior Publication Data

US 2005/0014290 A1      Jan. 20, 2005

Related U.S. Application Data

(63) Continuation-in-part of application No. 10/040,077, filed on Jan. 4, 2002, now Pat. No. 6,855,556.

(51) Int. Cl.
C07K 14/00 (2006.01)
A61K 38/00 (2006.01)

(52) U.S. Cl. .......................................... 530/350; 514/2
(58) Field of Classification Search ........................ None
See application file for complete search history.

(56) References Cited

U.S. PATENT DOCUMENTS

| | | | |
|---|---|---|---|
| 5,341,805 | A | 8/1994 | Stavridi et al. |
| 5,342,789 | A | 8/1994 | Chick et al. |
| 5,470,714 | A | 11/1995 | Kleinfeld |
| 5,517,313 | A | 5/1996 | Colvin, Jr. |
| 5,910,661 | A | 6/1999 | Colvin, Jr. |
| 6,197,534 | B1 | 3/2001 | Lakowicz et al. |
| 6,277,627 | B1 | 8/2001 | Hellinga |
| 6,521,446 | B2 | 2/2003 | Hellinga |
| 6,855,556 | B2 * | 2/2005 | Amiss et al. .................. 436/95 |
| 2002/0004217 | A1 | 1/2002 | Hellinga |
| 2003/0130167 | A1 | 7/2003 | Pitner et al. |
| 2003/0134346 | A1 | 7/2003 | Amiss et al. |
| 2003/0153026 | A1 | 8/2003 | Alarcon et al. |
| 2003/0232383 | A1 | 12/2003 | Daunert et al. |

FOREIGN PATENT DOCUMENTS

| | | |
|---|---|---|
| WO | WO9109310 A1 | 6/1991 |
| WO | WO9423284 A1 | 10/1994 |
| WO | WO 99/34212 | 7/1999 |
| WO | WO9934212 A1 | 7/1999 |
| WO | WO0003727 A1 | 1/2000 |

OTHER PUBLICATIONS

Bjorkman et al., Multiple Open Forms of Ribose-binding Protein Trace the Path of its Conformational Change. J. Mol. Biol. (1987) 279:651-64.

Boos et al., Transport Properties of the Galactose-Binding Protein of Escherichia Coli: Occurrence of Two Conformational States. J. Biol. Chem. (1971) 246:621-28.

Boos et al., Transport Properties of the Galactose-Binding Protein of Escherichia Coli:Substrate-Induced Conformational Change. J Biol. Chem. (1972) 247:917-24.

Boos W., Structurally defective galactose-binding protein isolated from a mutant negative in the B-methylgalactoside transport system of Escherichia coli. J. Biol. Chem., (1972) 247:5414-24.

Brune et al., Direct, Real-Time Measurement of Rapid Inorganic Phosphate Release Using a Novel Fluorescent Probe and Its Application to Actomyosin Subfragment 1 ATPase, Biochem. (1994) 33(27):8262-71.

Careaga et al., Large Amplitude Twisting Motions of an Interdomain Hinge: A Disulfide Trapping Study of the Galactose-Glucose Binding Protein, Biochemistry 34:3048-3055 (1995).

Careaga et al., Structure and Dynamics of Escherichia-Coli Chemosensory Receptors Engineered Sulfuydryl Studies. Biophysical Journal (1992) 62:209-19.

Careaga et al., Thermal Motions of Surface Alpha-Helices in the D-Galactose Chemosensory Receptor. Detection by Disulfide Trapping. J Mol. Biol. (1992) 226:1219-35.

Clarmont D. J., Biosensors: clinical requirements and scientific promise. J. Med. Eng.Tech. (1987) 2:51-56.

Drueckhammer D. G., New Approaches to Fluorescence Based Glucose Sensors, Database FEDRIP on Dialog, N111S, 00313296, Identifying No. 1R21DK55234-01, Abstract (1998).

Ge et al., Genetically Engineered Binding Proteins as Biosensors for Fermentation and Cell Culture. Biotech. Eng. (2003) 84:723.

Gilardi et al., Engineering the Maltose Binding Protein for Reagentless Fluorescence Sensing. Anal. Chem. (1994) 66:3840-47.

Gilardi et al., Spectroscopic Properties of an Engineered Maltose Binding Protein. Protein Engineering (1997) 10:479-86.

Kunkel, T. Oligonucleotide-Directed Mutagenesis without Phenotypic Selection. In Current Protocol. In Molecular Biology (Ausubel, F., Brent, R, Kingston, R E., Moore, D. D., Seidman, J. G., Smith, J. A., Struhl, K. eds.) (1991) 1:Section 8.1.1, Wiley and Sons, New York.

Lakowicz et al., Polarization-Based Sensing of Glucose Using an Oriented Reference Film. J. Biomed. Opt. (1999) 4:443-49.

Li et al., Comparative stereochemical analysis of glucose-binding proteins for rational design of glucose-specific agents, J. Biomater. Sci. Polymer Edn, (1998) 9(4):327-44.

Liang et al., Anatomy of Protein Pockets and Cavities: Measurement of Binding Site Geometry and Implications for Ligand Design. Protein Science (1998) 7:1884-97.

(Continued)

Primary Examiner—Anand U Desai
(74) Attorney, Agent, or Firm—Morgan, Lewis & Bockius, LLP

(57) ABSTRACT

The invention is directed to compositions of mutated binding proteins containing reporter groups, analyte biosensor devices derived therefrom, and their use as analyte biosensors both in vitro and in vivo.

9 Claims, 7 Drawing Sheets

OTHER PUBLICATIONS

Luck et al., 19F NMR Studies of the D-Galactose Chemosensory Receptor. 1. Sugar Binding Yields a Global Structural Change. Biochem. (1991) 30:4248-56.

Marvin et al., Engineering biosensors by introducing fluorescent allosteric signal transducers: Construction of a novel glucose sensor. J. Am. Chem. Soc., (1998) 120:7-11.

Marvin et al., Manipulation of Ligand Binding Affinity by Exploitation of Conformational Coupling. Nature Structural Biology (2001) 8:795-98.

Marvin et al., The rational design of allosteric interactions in a monomeric protein and its applications to the construction of biosensors, Proc. Natl. Acad. Sci. (1997) 94:4366-71.

Neu et al., The release of enzymes from *Escherichia coli* by osmotic shock and during the formation of spheroplasts. Journal of Biological Chemistry, (1965) 240:3685-91.

Pickup J., Developing glucose sensors for n vivo use, Trends in Bioctech. (1993) 11:285-91.

Quiocho et al., Atomic Structure and Specificity of Bacterial Periplasmic Receptors for Active Transport and Chemotaxis: Variation of Common Themes. Molecular Microbiology (1996) 20:17-25.

Russell et al., A Fluorescent Glucose Assay Using Poly-L-Lysine and Calcium Alginate Microencapsulated Tritc-Succinyl-Concanavalin A And Fitc-Dextran Proc. 20th Ann. International Conf. IEEE-EMBS, (1998) 20:2858.

Salins et al., A Novel Reagentless Sensing System for Measuring Glucose Based on the Galactose/Glucose-Binding Protein. Analytical Biochemistry 2001, 294:19-26.

Scholle et al., Sequence of the mgIBgene from *Escherichia coli* K12: Comparison of wild-type and mutant galatose chemoreceptors. Mol. Gen. Genet. (1987) 247-53.

Schultz et al., Affinity sensor: A new technique for developing implantable sensors for glucose and other metabolites. Diabetes Care (1982) 5:245-53.

Schultz et al., Affinity sensors for individual metabolites. Biotechnology and Bioengineering Symp. 9 (1979) 9:65-71.

Shilton et al., Conformational Changes of Three Periplasmic Receptors for Bacterial Chemotaxis and Transport: the Maltose-, Glucose/Galactose- and Ribose-binding Proteins. J. Mol. Biol. (1996) 265:350-63.

Tolosa et al., (1999). Glucose Sensor for Low-Cost Lifetime-Based Sensing Using a Genetically Engineered Protein. Anal. Biochem. (1999) 267:114.

Tolosa et al., Lifetime-based sensing of glucose using energy transfer with a long lifetime donor. Analytical Biochemistry (1997) 250:102-08.

Tolosa et al., Optical assay for glucose based on the luminescence decay tim: of the long wavelength dye Cy5. Sensors and Actuators, (1997) B45:93-99.

Tolosa et al., Optical Biosensors Based on Genetically-Engineered *E. Coli* Periplasmic Binding Proteins. Biophysics Journal (2000) 78:2453Poster, Part 2.

Turcatti et al., Probing the Structure and Function of the Tachykinin Neurokinin-2 Receptor Through Biosynthetic Incorporation of Fluorescent Amino Acids at Specific Sites. J. Biol. Chem. (1996) 271:9991-98.

Vyas et al., Crystallographic Analysis of the Epimeric and Anomeric Specificity of the Periplasmic Transport! Chemosensory Protein Receptor for D-GJucose and D-Galactose, Biochemistry (1994) 33:4762-68.

Wang et al., Fine-Tuning the Specificity of the Peliplasmic Phosphate-Transport Receptor—Site-Directed Mutagenesis, Ligand-Binding, and Crystallographic Studies. J. Bid. Chem. (1994) 269:25091-94.

Wilkins et al.,Glucose monitoring: state of the art and future possibilities, Med. Eng. Phys. (1996) 18(4):273-88.

Zhou et al., Periplasmic Binding Protein Based Biosensors. 1. Preliminary Study of Maltose Binding Protein as Sensing Element for Maltose Biosensor. Biosensors; Bioelectronics (1991) 6:445-450.

Zukin et al., Effect of an Induced Conformational Change on the Physical Properties of Two Chemotactic Receptor Molecules. Biochemistry (1979) 18:5599-605.

Zukin et al., Properties of the galactose binding protein of salmonella typhimurium and *Escherichia coli*. Biochemistry (1977) 16:381-86.

Zukin et al., Use of a Distant Reporter Group As Evidence for a Conformational Change in a Sensory Receptor. Proc. Natl. Acad. Sci. (1977) 74:1932-36.

Zukin, R. S.; Evidence for a Conformational Change in the *Escherichia coli* Maltose Receptor by Excited-State Fluorescence Lifetime Data. Biochemistry (1979) 18:2139-45.

Hsieh, Direct detection of glucose by surface plasmon resonance with bacterial glucose/galactose-binding protein, Biosensors and Bioelectronics, 19, No. 7, 2004, pp. 653-660.

International Search Report PCT/US2005/003127, Mailed May 2, 2005.

* cited by examiner

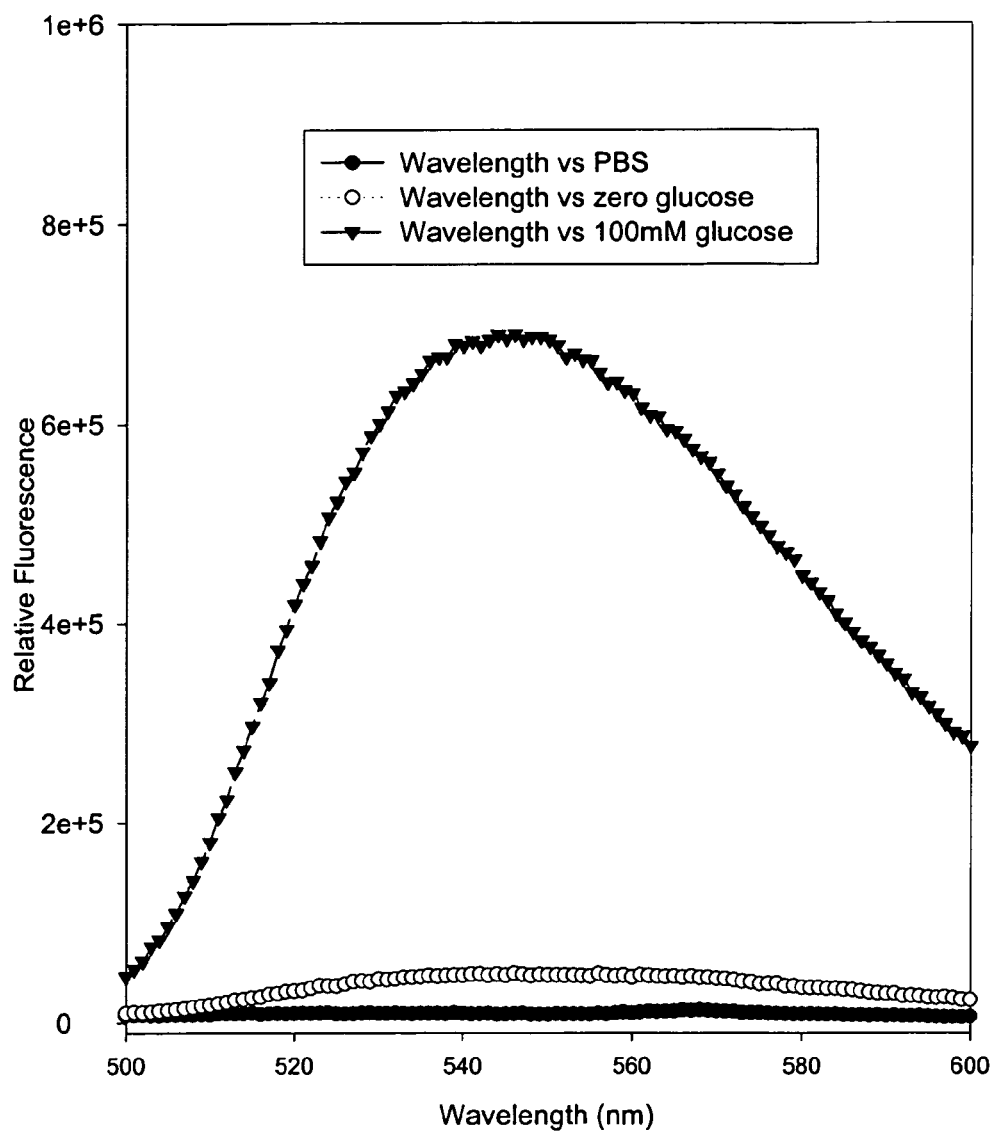
FIGURE 4 illustrates the change in fluorescence response to 100 mM glucose for E149C/A213C/L238S NBD amide GGBP $H_6$ in solution.

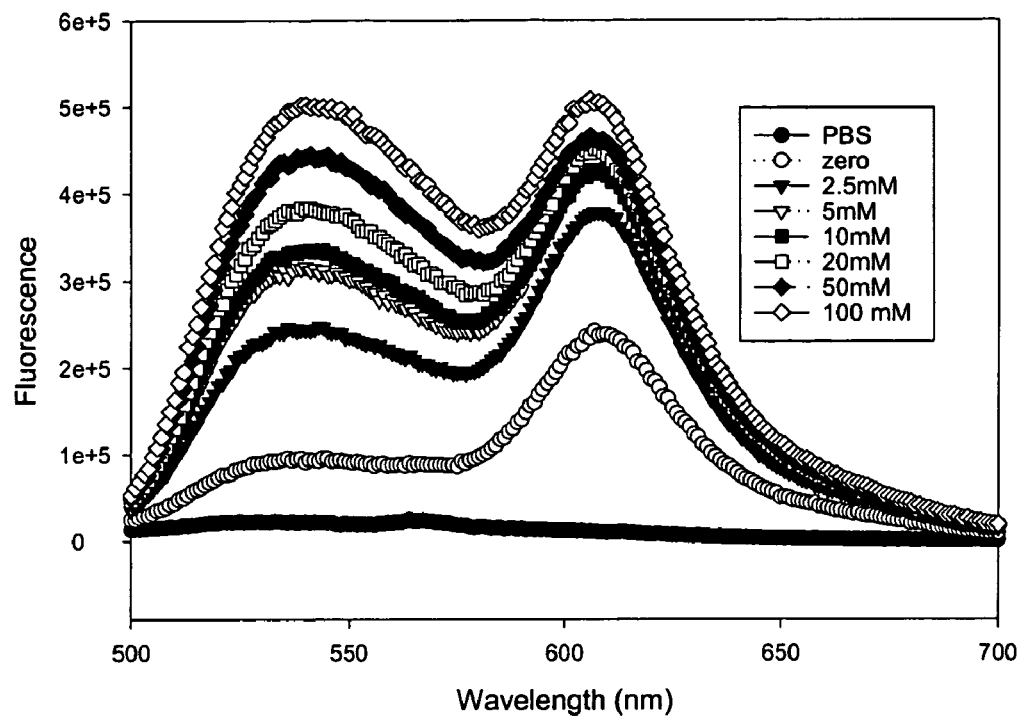
Figure 5 illustrates the change in fluorescence response to a range of glucose concentrations for E149C/A213C/L238S NBD / Texas Red GGBP $H_6$ in solution.

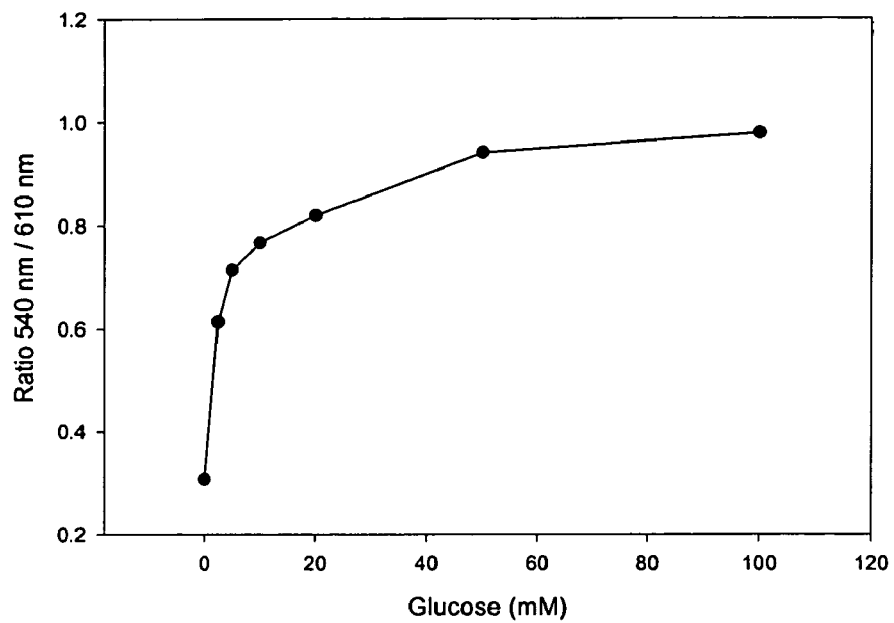
Figure 6 illustrates the change in fluorescence emission ratio (540 nm/610 nm) to a range of glucose concentrations for E149C/A213C/L238S NBD / Texas Red GGBP $H_6$ in solution.

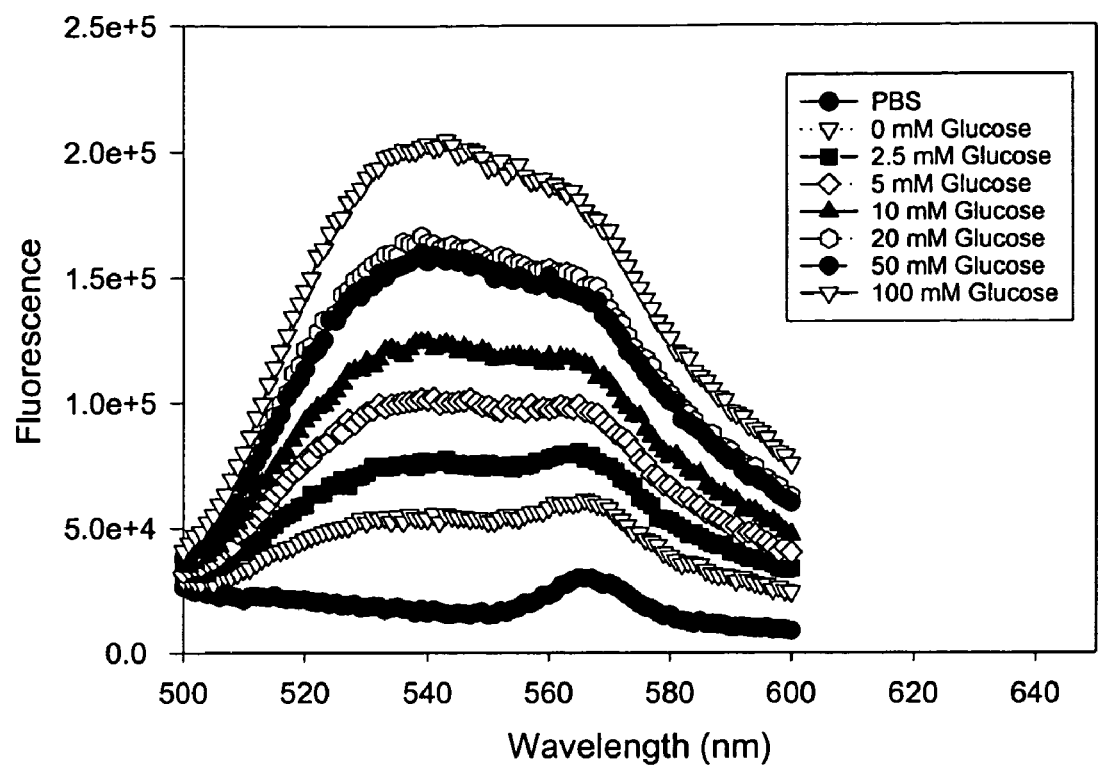
FIGURE 7 illustrates the change in fluorescence response to various concentrations of glucose for E149C/A213R/L238C NBD amide GGBP $H_6$ in solution.

BINDING PROTEINS AS BIOSENSORS

This application is a continuation-in-part of U.S. patent application Ser. No. 10/040,077 filed Jan. 4, 2002, the entire contents of which are incorporated by reference herein.

A computer readable text file, entitled "100496-5006-US01_SequenceListing.txt", created on or about Apr. 27, 2009 and having a size of about 4 kb contains the sequence listing of this application and is hereby incorporated by reference.

BACKGROUND OF THE INVENTION

1. Field of the Invention

The invention is in the field of biotechnology. Specifically, the invention is directed to compositions of mutated binding proteins containing reporter groups, analyte biosensor devices derived therefrom, and their use as analyte biosensors both in vitro and in vivo.

2. Description of Relevant Art

Monitoring glucose concentrations to facilitate adequate metabolic control in diabetics is a desirable goal and would enhance the lives of many individuals. Currently, most diabetics use the "finger stick" method to monitor their blood glucose levels and patient compliance is problematic due to pain caused by frequent (several times per day) sticks. As a consequence, there have been efforts to develop non-invasive or minimally invasive in vivo and more efficient in vitro methods for frequent and/or continuous monitoring of blood glucose or other glucose-containing biological fluids. Some of the most promising of these methods involve the use of a biosensor. Biosensors are devices capable of providing specific quantitative or semi-quantitative analytical information using a biological recognition element that is combined with a transducing (detecting) element.

The biological recognition element of a biosensor determines the selectivity, so that only the compound to be measured leads to a signal. The selection may be based on biochemical recognition of the ligand where the chemical structure of the ligand (e.g. glucose) is unchanged, or biocatalysis in which the element catalyzes a biochemical reaction of the analyte.

The transducer translates the recognition of the biological recognition element into a semi-quantitative or quantitative signal. Possible transducer technologies are optical, electrochemical, acoustical/mechanical or colorimetrical. The optical properties that have been exploited include absorbance, fluorescence/phosphorescence, bio/chemiluminescence, reflectance, light scattering and refractive index. Conventional reporter groups such as fluorescent compounds may be used, or alternatively, there is the opportunity for direct optical detection, without the need for a label.

Biosensors specifically designed for glucose detection that use biological elements for signal transduction typically use electrochemical or colorimetric detection of glucose oxidase activity. This method is associated with difficulties including the influence of oxygen levels, inhibitors in the blood and problems with electrodes. In addition, detection results in consumption of the analyte that can cause difficulties when measuring low glucose concentrations.

A rapidly advancing area of biosensor development is the use of fluorescently labeled periplasmic binding proteins (PBP's). As reported by Cass (Anal. Chem. 1994, 66, 3840-3847), a labeled maltose binding protein (MBP) was effectively demonstrated as a useable maltose sensor. In this work MBP, which has no native cysteine residues, was mutated to provide a protein with a single cysteine residue at a position at 337 (S337C). This mutation position is within the binding cleft where maltose binding occurred and therefore experiences a large environmental change upon maltose binding. Numerous fluorophores were studied, some either blocked ligand binding or interfered with the conformational change of the protein. Of those studied IANBD resulted in a substantial increase in fluorescence (160%) intensity upon maltose binding. This result is consistent with the location of the fluorophore changing from a hydrophilic or solvent exposed environment to a more hydrophobic environment as would have been theoretically predicted for the closing of the hinge upon maltose binding. However, this mutant protein and the associated reporter group do not bind diagnostically important sugars in mammalian bodily fluids. Cass also disclosed (Analytical Chemistry 1998, 70(23), 5111-5113) association of this protein onto $TiO_2$ surfaces, however, the surface-bound protein suffered from reduced activity with time and required constant hydration.

Hellinga, et al. (U.S. Pat. No. 6,277,627) reports the engineering of a glucose biosensor by introducing a fluorescent transducer into a Galactose/Glucose Binding Protein (GGBP) mutated to contain a cysteine residue, taking advantage of the large conformation changes that occur upon glucose binding. Hellinga, et. al. (U.S. Pat. No. 6,277,627) disclose that the transmission of conformational changes in mutated GGBPs can be exploited to construct integrated signal transduction functions that convert a glucose binding event into a change in fluorescence via an allosteric coupling mechanism. The fluorescent transduction functions are reported to interfere minimally with the intrinsic binding properties of the sugar binding pocket in GGBP.

In order to accurately determine glucose concentration in biological solutions such as blood, interstitial fluids, ocular solutions or perspiration, etc., it may be desirable to adjust the binding constant of the sensing molecule of a biosensor so as to match the physiological and/or pathological operating range of the biological solution of interest. Without the appropriate binding constant, a signal may be out of range for a particular physiological and/or pathological concentration. Additionally, biosensors may be configured using more than one protein, each with a different binding constant, to provide accurate measurements over a wide range of glucose concentrations as disclosed by Lakowicz (U.S. Pat. No. 6,197,534).

Despite the usefulness of mutated GGBPs, few of these proteins have been designed and examined, either with or without reporter groups. Specific mutations of sites and/or attachment of certain reporter groups may act to modify a binding constant in an unpredictable way. Additionally, a biosensor containing reporter groups may have a desirable binding constant, but not result in an easily detectable signal change upon analyte binding. Some of the overriding factors that determine sensitivity of a particular reporter probe attached to a particular protein for the detection of a specific analyte is the nature of the specific interactions between the selected probe and amino acid residues of the protein. It is not currently possible to predict these interactions within proteins using existing computational methods, nor is it possible to employ rational design methodology to optimize the choice of reporter probes. It is currently not possible to predict the effect on either the binding constant or the selectivity based on the position of any reporter group, or amino acid substitution in the protein (or vice-versa).

To develop reagentless, self-contained, and/or implantable and/or reusable biosensors using proteins the transduction element must be in communication with a detection device to interrogate the signal to and from the transduction element. By "interrogate" is meant the process of sending light to, and measuring emitted light from, a sample. Typical methods include placing proteins within or onto the surface of optical fibers or planner waveguides using immobilization strategies. Such immobilization strategies include entrapment of the protein within semi-permeable membranes, organic polymer matrixes, or inorganic polymer matrixes. The immobilization strategy may ultimately determine the performance of the working biosensor. The prior art details numerous problems associated with the immobilization of biological molecules. For example, many proteins undergo irreversible conformational changes, denaturation, and loss of biochemical activity. Immobilized proteins can exist in a large number of possible orientations on any particular surface, for example, with some proteins oriented such that their active sites are exposed whereas others may be oriented such that there active sites are not exposed, and thus not able to undergo selective binding reactions with the analyte. Immobilized proteins are also subject to time-dependent denaturation, denaturation during immobilization, and leaching of the entrapped protein subsequent to immobilization. Therefore, problems result including an inability to maintain calibration of the sensing device and signal drift. In general, binding proteins require orientational control to enable their use, thus physical absorption and random or bulk covalent surface attachment or immobilization strategies as taught in the literature generally are not successful.

Therefore, there is a need in the art to design additional useful mutated proteins and mutated GGBP proteins generating detectable signal changes upon analyte binding for use as biosensors, and additionally there is a need in the art to design additional useful mutated binding protein and mutated GGBPs containing reporter groups generating detectable and reversible signal changes upon analyte or glucose binding for use as biosensors.

SUMMARY OF THE INVENTION

The invention provides a glucose biosensor for in vivo or in vitro use having at least one mutated binding protein and at least one reporter group attached thereto such that said reporter group provides a detectable and reversible signal change when said mutated binding protein is exposed to varying glucose concentrations; and wherein said detectable and reversible signal change is related to said varying concentrations.

Furthermore, the invention provides a method for glucose detection including a) providing at least one mutated glucose/galactose binding protein and at least one reporter group attached thereto; b) exposing said mutated glucose/galactose binding protein to varying glucose concentrations; and c) detecting a detectable and reversible signal change from said reporter group wherein said detectable and reversible signal change corresponds to said varying glucose concentrations.

The invention additionally provides a composition including a mutated glucose/galactose binding protein having at least one amino acid substitution selected from the group consisting of cysteine at position 1 or a serine at position 1, a cysteine at position 11, a cysteine at position 14, a cysteine at position 19, a cysteine at position 43, a cysteine at position 74, a cysteine at position 107, a cysteine at position 110, a cysteine at position 112, a cysteine at position 113, a cysteine at position 137, a cysteine at position 149, a cysteine at position 213, a cysteine at position 216, a cysteine at position 238, a cysteine at position 287, a cysteine at position 292, a cysteine at position 152, a cysteine at position 182, a cysteine at position 236, and a cysteine at position 296.

Also provided herein is a composition having a mutated glucose/galactose binding protein having at least two amino acid substitutions selected from the group consisting of a cysteine at position 112 and a serine at position 238; a cysteine at position 149 and a cysteine at position 238; a cysteine at position 149 and a serine at position 238; a cysteine at position 152 and a serine at position 213; a cysteine at position 213 and a cysteine at position 238; a cysteine at position 149 and an arginine at position 213; a cysteine at position 149, a serine at position 213, and a serine at position 238; a cysteine at position 149, an arginine at position 213, and a cysteine at position 238 and a cysteine at position 149, an arginine at position 213, and a serine at position 238. Additional examples of mutated glucose/galactose binding proteins are shown hereinbelow in Table 1. Amino acid residue numbers refer to the published sequence of *E. coli* having 309 residues, as detailed below, or the corresponding amino acid residue in any substantially homologous sequence from an alternative source (e.g., glucose/galactose binding proteins from *Citrobacter freundii* or *Salmonella typhimurium*, sequence accession numbers P23925 and P23905, respectively).

BRIEF DESCRIPTION OF THE DRAWINGS

FIG. 4 illustrates the change in fluorescence response to a range of glucose concentrations for E149C/A213C/L238S NBD amide GGBP $H_6$ solution.

FIG. 5 illustrates the change in fluorescence emission for a solution of NBD-TR-CCS upon addition of varying amounts of glucose.

FIG. 6 is a plot of the emission ratio of NBD and Texas Red using the emission spectra from FIG. 5.

FIG. 7 illustrates the change in fluorescence emission upon adding 100 mM glucose to a solution of E149C/A213R/L238C GGBP labeled with two NBD molecules.

DETAILED DESCRIPTION OF THE INVENTION

Figure 1:
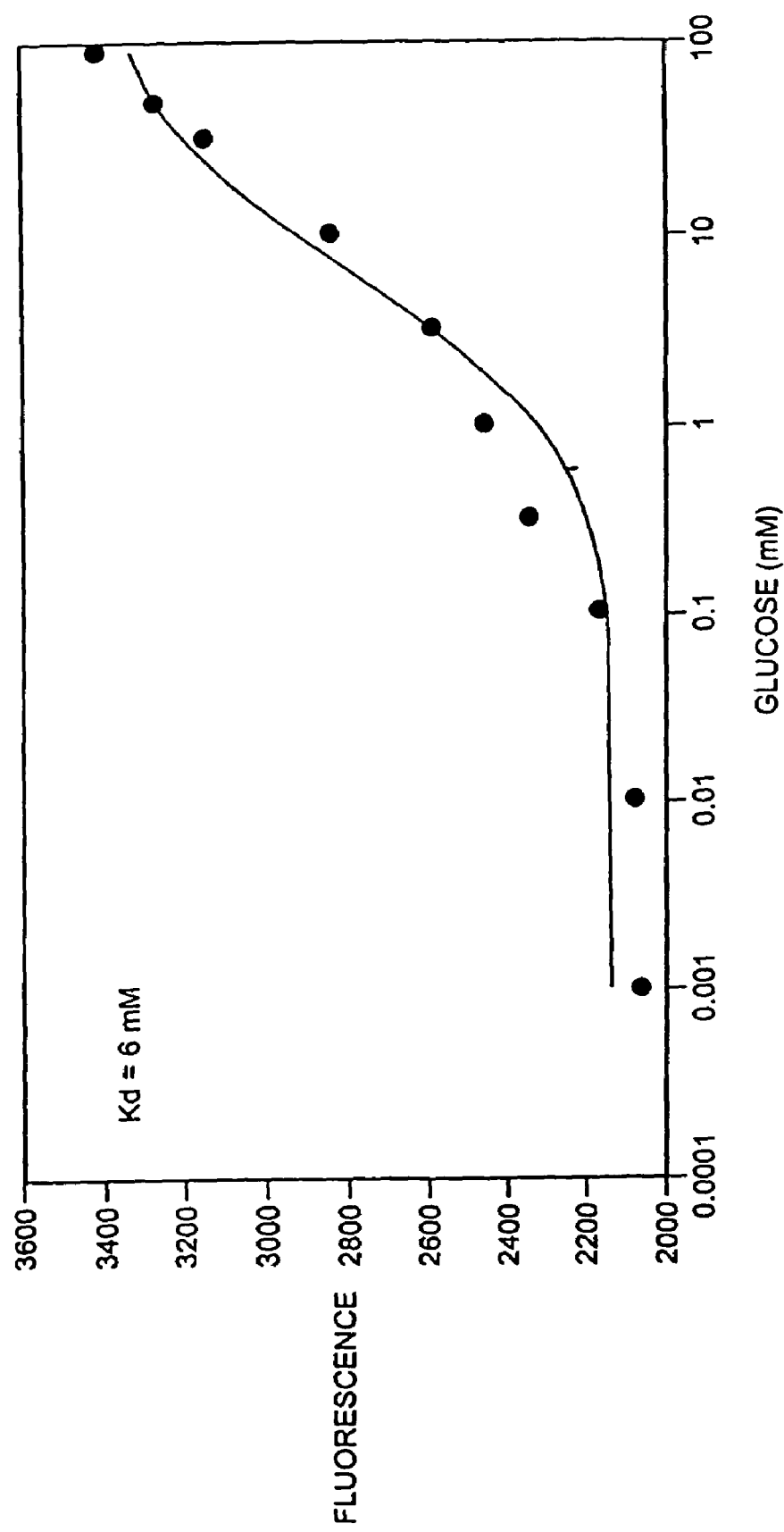
FIG. 1 illustrates the change in fluorescence response to a range of glucose concentrations for A213C/L238C NBD amide GGBP $H_6$ in solution.

The term biosensor generally refers to a device that uses specific biochemical reactions mediated by isolated enzymes, immunosystems, tissues, organelles or whole cells to detect chemical compounds, usually by electrical, thermal or optical signals. As used herein, a "biosensor" refers to a protein capable of binding to an analyte that may be used to detect an analyte or a change in analyte concentration by a detector means as herein described.

The term "binding proteins" refers to proteins that interact with specific analytes in a manner capable of providing or transducing a detectable and/or reversible signal differentiable either from when analyte is not present, analyte is present in varying concentrations over time, or in a concentration-dependent manner, by means of the methods described herein. The transduction event includes continuous, programmed, and episodic means, including one-time or reusable applications. Reversible signal transduction may be instantaneous or may be time-dependent providing a correlation with the presence or concentration of analyte is established. Binding proteins mutated in such a manner to effect transduction are preferred.

The term "Galactose/Glucose Binding Protein" or "GGBP" as used herein refers to a type of protein naturally found in the periplasmic compartment of bacteria. These proteins are naturally involved in chemotaxis and transport of small molecules (e.g., sugars, amino acids, and small peptides) into the cytoplasm. GGBP is a single chain protein consisting of two globular α/β domains that are connected by three strands to form a hinge. The binding site is located in the cleft between the two domains. When glucose enters the binding site, GGBP undergoes a conformational change, centered at the hinge, which brings the two domains together and entraps glucose in the binding site. X-ray crystallographic structures have been determined for the closed form of GGBP from coli (N. K. Vyas, M. N. Vyas, F. A. Quiocho Science 1988, 242, 1290-1295) and S. Typhhnuriwn (S. L. Mowbray, R. D. Smith, L. U. Cole Receptor 1990, 1, 41-54) and are available from the Protein Data Bank available on the world wide web at www.resb.org/pdb/ as 2 GBP and 3 GBP, respectively. The wild type E. coli GGBP DNA and amino acid sequence can be found at www.ncbi.nlm.nih.gov/entrez/accession number D90885 (genomic clone) and accession number 230520 (amino acid sequence). Preferred GGBP is from E. coil.

"Mutated Binding Protein" (for example "mutated GGBP") as used herein refers to binding proteins from bacteria containing an amino acid(s) that has been substituted for, deleted from, or added to the amino acid(s) present in naturally occurring protein. Preferably such substitutions, deletions or insertions involve fewer than 5 amino acid residues, or more preferably one to three residues. Exemplary mutations of binding proteins include the addition or substitution of cysteine groups, non-naturally occurring amino acids (Turcatti, et at. *J Bio, Chem.* (1996) 271, 33, 19991-19998) and replacement of substantially non-reactive amino acids with reactive amino acids to provide for the covalent attachment of electrochemical or photo-responsive reporter groups. By "reactive" amino acid is meant an amino acid that can be modified with a labeling agent analogous to the labeling of cysteine with a thiol reactive dye. Non-reactive amino acids include alanine, leucine, phenylalanine, and others, which possess side chains which cannot be readily modified once incorporated in a protein (see Greg T. Hermanson, Bioconjugate Techniques, Academic Press, 1996, San Diego, pp. 4-16 for classification of amino acid side chain reactivity).

Exemplary mutations of the *E. coli* GGBP protein include a cysteine substituted for a lysine at position 11 (K11C); a cysteine substituted for aspartic acid at position 14 (D14C); a cysteine substituted for valine at position 19 (V19C); a cysteine substituted for asparagine at position 43 (N43C); a cysteine substituted for glycine at position 74 (C74C); a cysteine substituted for tyrosine at position 107 (Y107C); a cysteine substituted for threonine at position 110 (T110C); a cysteine substituted for serine at position 112 (S112C); a double mutant including a cysteine substituted for serine at position 112 and serine substituted for leucine at position 238 (S112C/L238S); a cysteine substituted for lysine at position 113 (K113C); a cysteine substituted for lysine at position 137 (K137C); a cysteine substituted for glutamic acid at position 149 (B149C); a double mutant including a cysteine substituted for glutamic acid at position 149 and a cysteine substituted for leucine at position 238 (E149C/L238C); a double mutant including a cysteine substituted for glutamic acid at position 149 and a serine substituted for leucine at position 238 (E149C/L238S); a double mutant including a serine substituted for alanine at position 213 and a cysteine substituted for histidine at position 152 (H152C/A213S); a cysteine substituted for methionine at position 182 (M182C); a cysteine substituted for alanine at position 213 (A213C); a double mutant including a cysteine substituted for alanine at position 213 and a cysteine substituted for leucine at position 238 (A213C/L238C); a cysteine substituted for methionine at position 216 (M216C); a cysteine substituted for aspartic acid at position 236 (D236C); a cysteine substituted for leucine at position 238 (L238C); a cysteine substituted for aspartic acid at position 287 (D287C); a cysteine substituted for arginine at position 292 (R292C); a cysteine substituted for a valine at position 296 (V296C); a triple mutant including a cysteine substituted for glutamic acid at position 149, an alanine substituted for serine at position 213 and a serine substituted for leucine at position 238 (E149C/A213S/L238S); a triple mutant including a cysteine substituted for glutamic acid at position 149, an arginine substituted for an alanine at position 213 and a serine substituted for leucine at position 238 (E149C/A213R/L238S); a triple mutant including a cysteine substituted for glutamic acid at position 149, a cysteine substituted for alanine at position 213 and a cysteine substituted for leucine at position 238 (E149C/A213C/L238C); a triple mutant including a cysteine substituted for glutamic acid at position 149, a cysteine substituted for alanine at position 213 and an asparagine for lysine at position 223 (E149C/A213C/K223N); a triple mutant including a cysteine substituted for glutamic acid at position 149, an asparagines for lysine at position 223 and an arginine for asparagine at position 256 (E149C/K223N/N256R); a triple mutant including a cysteine substituted for glutamic acid at position 149, an arginine substituted for alanine at position 213 and a cysteine substituted for leucine at position 238 (E149C/A213R/L238C); and in a particularly preferred embodiment, a triple mutant including a cysteine substituted for glutamic acid at position 149, a cysteine substituted for alanine at position 213 and a serine substituted for leucine at position 238 (E149C/A213C/L238S). Quadruple (and higher) mutants are also included, for example a mutant in which serine replaces alanine at position 1, cysteine replaces glutamic acid at position 149, arginine replaces alanine at position 213 and serine replaces leucine at position 238 (A1S/E149C/A213R/L238S); a mutant in which serine replaces alanine at position 1, cysteine replaces glutamic acid at position 149, serine replaces alanine at position 213 and serine replaces leucine at position 238 (A1S/E149C/A213S/L238S); and a mutant in which cysteine replaces glutamic acid at position 149, cysteine replaces methionine at position 182, cysteine replaces alanine at position 213 and serine replaces leucine at position 238 (E149C/M182C/A213C/L238S).

The mutation may serve one or more of several purposes. For example, a naturally occurring protein may be mutated in order to change the long-term stability of the protein; to conjugate, bind, couple or otherwise associate the protein to a particular encapsulation matrix or polymer; to provide binding sites for detectable reporter groups; to adjust its binding constant with respect to a particular analyte; or any combination thereof.

In the instant invention, analyte and mutated protein act as binding partners. The term "associates" or "binds" as used herein refers to binding partners having a relative binding constant ($K_d$) sufficiently strong to allow detection of binding to the protein by a detection means. The $K_d$ may be calculated as the concentration of free analyte at which half the protein is bound, or vice versa. When the analyte of interest is glucose, the $K_d$ values for the binding partners are preferably between about 0.0001 mM to about 30 mM, more preferably, the $K_d$ values range from about 1 mM to 15 mM in the instant invention.

In the present invention, it has been shown that mutated GGBPs may be used to detect glucose binding by attaching thereto a reporter group that tranduces a detectable signal change upon glucose binding. To "provide a detectable signal change", as used herein, refers to the ability to recognize a change in a property of a reporter group in a manner that enables the detection of ligand-protein binding. For example, in one embodiment, the mutated GGBPs comprise a detectable reporter group whose detectable characteristics alter upon a change in protein conformation that occurs on glucose binding. In a preferred embodiment, the reporter group is a luminescent label that results in a mutated GGBP with an affinity for glucose producing a detectable shift in luminescence characteristics on glucose binding. The change in the detectable characteristics may be due to an alteration in the environment of the label, which is bound to the mutated GGBP.

The luminescent label may be a fluorescent label or a phosphorescent label. The use of fluorescent labels that may be excited to fluoresce by exposure to certain wavelengths of light is preferred.

In one embodiment, the reporter group is a fluorophore. As used herein, "fluorophore" refers to a molecule that absorbs energy and then emits light. Non-limiting examples of fluorophores useful as reporter groups in this invention include fluorescein, coumarins, rhodamines, 5-TMRIA (tetramethyl-rhodamine-5-iodoacetamide), (9-(2(or 4)-(N-(2-maleimdyl-ethyl)-sulfonamidyl)-4(or 2)-sulfophenyl)-2,3,6,7,12,13,16,17-octahydro-(1H,5H,11H,15H-xantheno(2,3,4-ij:5,6,7-i'j') diquinolizin-18-ium salt) (also known as Texas Red™), 2-(5-(1-(6-(N-(2-maleimdylethyl)-amino)-6-oxohexyl)-1,3-dihydro-3,3-dimethyl-5-sulfo-2H-indol-2-ylidene)-1,3-propyldienyl)-1-ethyl-3,3-dimethyl-5-sulfo-3H-indolium salt (also known as Cy™3), N-((2-iodoacetoxy)ethyl)-N-methyl)amino-7-nitrobenzoxadiazole (IANBD), 6-acryloyl-2-dimethylaminonaphthalene (acrylodan), pyrene, 6-amino-2,3-dihydro-2-(2-((iodoacetyl)amino)ethyl)-1,3-dioxo-1H-benz(de)isoquinoline-5,8-disulfonic acid salt (lucifer yellow iodoacetamide), 2-(5-(1-(6-(N-(2-maleimdylethyl)-amino)-6-oxohexyl)-1,3-dihydro-3,3-dimethyl-5-sulfo-2H-indol-2-ylidene)-1,3-pentadienyl)-1-ethyl-3,3-dimethyl-5-sulfo-3H-indolium salt (also known as Cy™5), 4-(5-(4-dimethylaminophenyl)oxazol-2-yl)phenyl-N-(2-bromoacetamidoethyl)sulfonamide (also known as Dapoxyl® (2-bromoacetamidoethyl)sulfonamide), (N-(4,4-difluoro-1,3,5,7-tetramethyl-4-bora-3a,4a-diaza-s-indacene-2-yl)iodoacetamide (also known as BODIPY® 507/545 IA), N-(4,4-difluoro-5,7-diphenyl-4-bora-3a,4a-diaza-s-indacene-3-propionyl)-N'-iodoacetylethylenediamine (also known as BODIPY® 530/550 IA), 5-((((2-iodoacetyl)amino)ethyl) amino)naphthalene-1-sulfonic acid (1,5-IAEDANS), and carboxy-X-rhodamine, 5/6-iodoacetamide (XRIA 5,6). Preferably, IANBD is used. Many detectable intrinsic properties of a fluorophore reporter group may be monitored to detect glucose binding. Some properties that can exhibit changes upon glucose binding include fluorescence lifetime, fluorescence intensity, fluorescence anisotropy or polarization, and spectral shifts of fluorescence emission. Changes in these fluorophore properties may be induced from changes in the fluorophore environment such as those resulting from changes in protein conformation. Environment-sensitive dyes such as IANBD are particularly useful in this respect. Other changes of fluorophore properties may result from interactions with the analyte itself or from interactions with a second reporter group, for example when FRET (fluorescence resonance energy transfer) is used to monitor changes in distance between two fluorophores.

Although the use of fluorescent labels is desired, it is contemplated that other reporter groups may be used. For example, electrochemical reporter groups can be used wherein an alteration in the environment of the reporter will give rise to a change in the redox state thereof. Such a change may be detected using an electrode.

Furthermore, it is envisaged that other spectroscopically detectable labels, for example labels detectable by NMR (nuclear magnetic resonance), may be used, as are known in the art.

The reporter group may be attached to the mutated protein or GGBPs by any conventional means known in the art. For example, the reporter group may be attached via amines or carboxyl residues on the protein. However, especially preferred is covalent coupling via thiol groups on cysteine residues. For example, for mutated GGBP, cysteines located at position 11, position 14, position 19, position 43, position 74, position 107, position 110, position 112, position 113, position 137, position 149, position 152, position 213, position 216, position 238, position 287, and position 292 are preferred in the present invention.

Any thiol-reactive group known in the art may be used for attaching reporter groups such as fluorophores to a cysteine of an engineered protein. For example, an iodoacetamide bromoacetamide, or maleimide are well known thiol-reactive moieties that may be used for this purpose.

Fluorophores that operate at long excitation and emission wavelengths (for example, about 600 nm or greater excitation or emission wavelengths) are preferred when the molecular sensor is to be used in vivo, for example, incorporated into an implantable biosensor device (the skin being opaque below 600 nm). Presently, there are few environmentally sensitive probes available in this region of the spectrum and perhaps none with thiol-reactive functional groups. However, thiol-reactive derivatives of Cy-5 can be prepared, for example, as taught by H. J. Gruber, et al, *Bioconjugate Chem.*, (2000), 11, 161-166. Conjugates containing these fluorophores, for example, attached at various cysteine mutants constructed in mutated GGBPs, can be screened to identify those that result in the largest change in fluorescence upon glucose binding.

Mutated GGBPs may be engineered to have a histidine tag on the proteins N-terminus, C-terminus, or both. Histidine fusion proteins are widely used in the molecular biology field to aid in the purification of proteins. Exemplary tagging systems produce proteins with a tag containing about six histidines and preferably such tagging does not compromise the binding activity of the mutated GGBP.

The present invention also provides a biosensor and method of using the biosensor for analyte sensing in vivo. In this aspect, the biosensor is comprised of one or more mutated binding proteins that are encapsulated into a matrix. The encapsulated biosensor may then be used as an implantable device or part thereof.

The "matrix" can be in any desirable form or shape including a disk, cylinder, patch, microsphere, porous polymer, open cell foam or the like, providing it is permeable to analyte. The matrix additionally prevents leaching of the biosensor. The matrix permits light from optical sources or any other interrogating light to or from the reporter group to pass through the biosensor. When used in an in vivo application, the biosensor will be exposed to a physiological range of analyte. The means of determination or detection of a change in analyte concentration may, in one embodiment, be continuous. Alternatively, the means of determination or detection of analyte concentration may be programmed or episodic.

The envisioned in vivo biosensor of the present invention comprises at least one mutated binding protein in an analyte permeable entrapping or encapsulating matrix such that the mutated binding protein provides a detectable and reversible signal change when the mutated binding protein is exposed to varying analyte concentrations, and the detectable and reversible signal can be related to the concentration of the analyte.

In this aspect of the invention, the configuration of the transducing element may be, for example, incorporated at the distal end of a fiber or other small minimally invasive probe and be inserted within the tissue of a patient to enable methods of use including episodic, continuous, or programmed reading, to the patient. The implantable biosensors may, in some embodiments, be implanted into or below the skin of a mammal's epidermal-dermal junction to interact with the interstitial fluid, tissue, or other biological fluids.

An exemplary method that may be used to detect the presence of analyte using the biosensor for in vivo use described herein includes interrogating the implant with a remote light source, detecting the signal from the protein-reporter group, and determining the amount of glucose based on a relationship to the detected signal as is known in the art (see U.S. Pat. No. 5,517,313, U.S. Pat. No. 5,910,661, and U.S. Pat. No. 5,342,789, all of which are herein incorporated by reference).

The binding protein biosensors of this invention are capable of measuring or detecting micromolar ($10^{-6}$ molar) to molar analyte concentrations without reagent consumption. In some embodiments, their sensitivity to analyte may enable the biosensors to be used to measure the low analyte concentrations known to be present in low volume samples of interstitial or ocular fluid and perspiration. The binding protein biosensors of the present invention provide for the means to monitor analyte continuously, episodically, or "on-demand" as would be appropriate to the user or to the treatment of a condition.

In other embodiments, the biosensors sensitivity to analyte (for example glucose) is such that they may be used to test blood analyte levels or the concentration of analyte in a biological solution or other solution may be determined. As used herein, a "biological solution" includes but is not limited to blood, perspiration, and/or ocular or interstitial fluid including combinations thereof.

The following examples illustrate certain preferred embodiments of the instant invention, but are not intended to be illustrative of all embodiments.

Example 1

Method for the Expression and Purification of Mutant Proteins without Histidine Tags GGBP is coded by the Mg1B-1 gene in E. coli. This protein was altered by introducing the amino acid cysteine at various positions through site-directed mutagenesis of the Mg1B-1 gene. These proteins were then expressed in E. coli and purified.

Cassette mutagenesis of Mg1B-1 was accomplished as follows. The wild-type Mg1B-1 gene was cloned into a pTZ18R vector (Dr. Anthony Cass, Imperial College, London, England). Mutant plasmids were generated from this parent plasmid using cassette mutagenesis producing randomized amino acid sequences, essentially as described by Kunkel (1991) and cloned in E. coli JM109 (Promega Life Science, Madison, Wis.). Mutant plasmids were identified by sequencing. The mutant protein was induced in JM109 and purified as described below. An E. coli JM109 colony containing the mutant plasmid was grown overnight at 37° C. with shaking (220 rpm) in LB broth containing 50 µg/mL ampicillin (LB/Amp). The overnight growth was diluted 1:100 in IL fresh LB/Amp and was incubated at 37° C. with shaking until the $OD_{600}$ of the culture was 0.3-0.5. Expression of the mutant was induced by the addition of 1 mM IPTG (Life Technologies, Gaithersburg, Md.) final concentration with continued incubation and shaking at 37° C. for 4-6 hours. The cells were harvested by centrifugation (10,000×g, 10 min, 4° C.).

The mutant protein was harvested by osmotic shock and was purified by column chromatography. The cell pellet was resuspended in a sucrose buffer (30 mM Tris-HCL pH 8.0, 20% sucrose, 1 mM EDTA), incubated at room temperature for 10 min, and then centrifuged (4000×g, 15 min, 4° C.). The supernatant was poured off and kept on ice. The cell pellet was resuspended, and 10 mL ice cold, sterile deionized $H_2O$ was repeated, and the suspension was incubated on ice and centrifuged. The remaining supernatant was pooled with the other collected supernatants and was centrifuged once again (12,000×g, 10 min, 4° C.). The pooled shockate was filtered through a 0.8 µm and then a 0.45 µm filter. Streptomycin sulfate (Sigma Chemical Co., St. Louis, Mo.), 5% w/v, was added to the shockate and was stirred once for 30 min followed by centrifugation (12,000×g, 10 min, 4° C.). The shockate was then concentrated using the Amicon Centriprep 10 (10,000 MWCO) filters (Charlotte, N.C.) and dialyzed overnight against 5 mM Tris-HCl pH 8.0, 1 mM $MgCl_2$. The dialyzed shockate was centrifuged (12,000×g, 30 min, 4° C. The resulting supernatant was added to a pre-equilibrated DEAE Fast Flow Sepharose column (Amersham Pharmacia Biotech, Piscataway, N.J.) at 0.5 mL/min. The column was washed with 5-10 column volumes. A linear gradient from 0-0.2 M NaCl was applied to the column and fractions were collected. The mutant protein containing fractions were identified by SDS-PAGE with Coomassie Brilliant Blue staining (mw. Approx. 32 kDa). The fractions were pooled and dialyzed overnight (4° C.) against phosphate buffered saline (PBS) or 10 mM ammonium bicarbonate (pH 7.4) concentrated using Amicon Centriprep 10 filters, and stored at 4° C. or −20° C. with glycerol. The ammonium bicarbonate dialyzed protein was lyophilized.

Example 2

Expression and Purification of Mutant GGBPs Containing Histidine Tags

GGBP mutants were engineered by either site-directed mutagenesis or cassette mutagenesis. Site-directed mutagenesis (QuikChange, Stratagene, La Jolla, Calif.) was performed to alter individual amino acids in the pQE70 vector by replacing one amino acid with another, specifically chosen amino acid. The cassette mutagenesis method (Kunkel 1991) was performed to randomize amino acids in a specified region of the GGBP gene. The mutated cassettes were then subcloned into the pQE70 expression vector.

The pGGBP-His plasmid contained the GGBP gene cloned into the pQE70 expression vector (Qiagen, Valencia, Calif.). This construct places six histidine residues on the C-terminus of the GGBP gene. E. coli strain SG13009 was used to overexpress mutant GGBP-His following standard procedures (Qiagen). After overexpression of a 250 mL culture, the cells were collected by centrifugation (6000 rpm) and resuspended in 25 mL Bugbuster™ (Novagen, Madison, Wis.). Lysozyme (25 mg was added to the lysate and the mixture was gently mixed at room temperature (RT) for 30 min. Clear lysate was produced by centrifugation (6000 rpm) and to this, 0.5 ml imidizole (1 M) and 3 ml of NI-NTA beads (Qiagen) was added. After 30 minutes of gently mixing at RT, the mixture was centrifuged (6000 rpm) and the lysate removed. The beads were washed with 25 ml of solution (1 M NaCl, 10 mM Tris, pH 8.0) and recentrifuged. The mutant GGBP-His was eluted from the beads by adding 5 mL solution (160 mM imidazole, 1 M NaCl, 10 mM Tris, pH 8.0) and mixing for 15 min. The protein solution was immediately filtered through a Centriplus YM-100 filter (Amicon, Charlotte, N.C.) and then concentrated to 1-3 mg/ml using a Centriplus YM-10 filter. The protein was dialyzed overnight against 2 L of storage solution (1 M NaCl, 10 mM Tris, 50 mM $NaPO_4$, pH 8.0).

Example 3

Labeling of Mutant GGBPs

Figure 2:
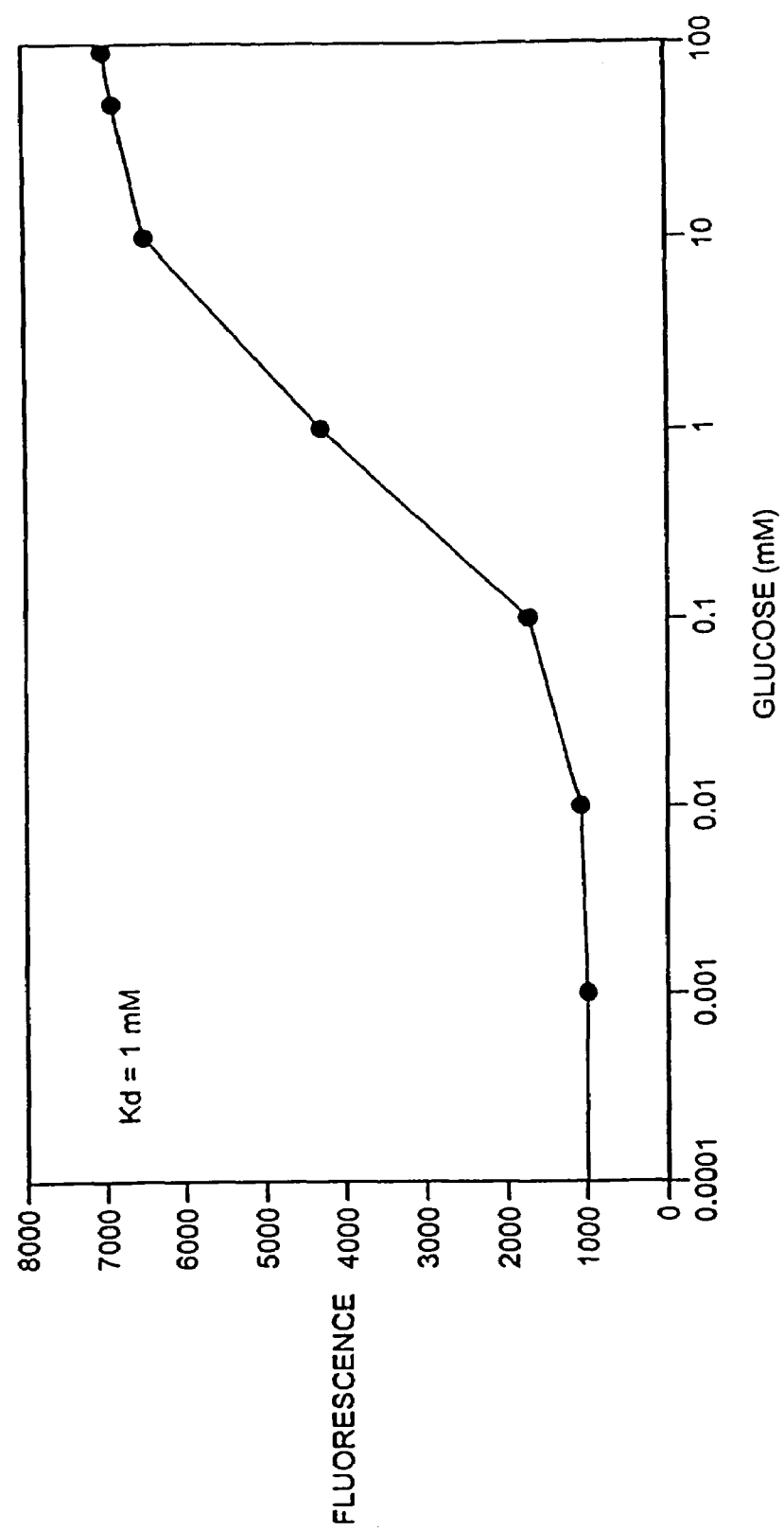
FIG. 2 illustrates the change in fluorescence response to a range of glucose concentrations for E149C/A213R NBD amide GGBP $H_6$ in solution.

An aliquot of mutant GGBP containing cysteine (4.0 mmol) in PBS was treated with 2 mM dithiothreitol (5 µL, 10 nmol) for 30 min. A stock solution of N,N'-dimethyl-N-(iodoacetyl)-N'-(7-nitrobenz-2-oxa-1,3-diazol-4-yl)ethylenediamine (IANBD amide, 0.5 mg) was prepared in DMSO (100 µL, 11.9 mM) and 3.36 µL (40 nmol) was added to the protein. The reaction proceeded at room temperature for 4 h on a Dynal rotamix in the dark. The labeled protein was purified by gel filtration on a NAP-5 column (Amersham Pharmacia). The labeling ratios were determined using an estimated extinction coefficient (50 $mM^{-1}$ $cm^{-1}$) for GGBP that was calculated in GeneWorks 2.45 (IntelliGenetics), $\epsilon_{478}$ (IANBD amide)=25 $mM^{-1}$ $cm^{-1}$), and a measurement of O.D. for a standard solution of IANBD amide at 280 nm and 478 nm. The dye concentration in the protein was calculated as $C_{dye}=A_{478}/\epsilon_{478}$. The absorbance of protein at 280 nm was calculated as $A_{prot(280)}=A_{total(280)}-A_{dye(280)}$, where $A_{dye(280)}=A_{478}\times(A_{280}/A_{478})_{dye\,std}$. The concentration of protein was then $C_{prot(280)}=A_{prot(280)}/\epsilon_{280}$. Table 1 summarizes the change in fluorescence of various GGBP mutants labeled with reporter groups, including reporting groups having either excitation or emission maximum of at least 600 nanometers. Table 2 summarizes the change in fluorescence, and determined $K_d$ values of mutations of one, two, three, and four amino acid substitutions. This data clearly shows mutations of GGBP labeled with reporter group can provide desirable attributes as glucose biosensors. The data shows the mutation-reporter group relationship for the samples tested. FIG. 1 illustrates the change in fluorescence response to various glucose concentrations of A213C/L238C NBD amide GGBP $H_6$, as a representative example, in solution. FIG. 2 illustrates the change in fluorescence response to various glucose concentrations of E149C/A213R NBD amide GGBP $H_6$, as yet another representative example, in solution.

TABLE 1

Percent Change in Fluorescence for GGBP Mutants[1]

| Dye | Excitation/ Emission (nm) | S112C | M182C | A213C | A213C $His_6$ | M216C |
|---|---|---|---|---|---|---|
| IANBD amide | 470/550 | 0 | 4 | 3 | 51 | 7 |
| IAEDANS | 336/490 | −7 | −8 | 0 |  | −9 |
| Bodipy530/550 IA | 530/550 | 7 | −10 | 33 |  | 4 |
| XRIA 5, 6 | 575/600 | −21 | −19 | −38 |  | −15 |
| Lucifer Yellow IA | 426/530 |  |  | −14 |  | −3 |
| Bodipy 507/545 IA | 507/545 |  |  | 25 |  | −3 |
| Cy5 | 640/660 | 2 | 0 | 11 |  | −7 |
| Texas Red-maleimide | 580/610 |  |  |  | −13 |  |
| Dapoxyl | 375/580 | 15 | 7 | 12 |  | 2 |

[1]F from 0 to 1 mM glucose at 0.5 uM [dye]. Unless otherwise indicated all mutants were w/o histidine tags.

Example 4

Detectable Signal Change Evident Upon Glucose Binding to the Mutated GGBP Labeled with Luminescent Labels and the Determination of $K_d$ The change in fluorescence (ΔF, Table 2) was measured as the percent difference in fluorescence between 0 and 1 mM glucose at either 0.5 µM protein concentration using an SLM Aminco fluorimeter (Ontario, Canada) with slit settings of 8 and 4 for excitation and settings of 5 and 5 on the MC250 emission monochromator or at 0.1 µM to 2 µM protein concentration in a PTI fluorometer.

Binding constants (Table 2) were determined by titration of increasing concentrations of glucose into a 0.1 µM protein solution (PBS) with mixing following each addition of glucose. Alternatively, samples with the same protein concentration and varying amounts of glucose were prepared. Slit settings were the same as listed above. The $K_d$ was determined from the following relationships as adapted from Pisarchick and Thompson (1990):

$$F = \frac{F_{inf} + F_0 - F_{inf}}{1 + x/Kd} \quad (1)$$

where F is fluorescence intensity, $F_{inf}$ is fluorescence at infinity, $F_0$ is fluorescence at zero glucose, and x is the free concentration of glucose ($[Glc]_{free}$) as determined by the relationship:

$$[GLc]_{free} = \frac{[GLC]_{tot} - [Prot]_{tot} - Kd + \sqrt{([Glc]_{tot} - [Prot]_{tot} - Kd)^2 + 4*[Glc]_{tot}*Kd}}{2}$$

where $[Glc]_{tot}$ and $[Pro]_{tot}$ are the total concentrations of glucose and protein, respectively. Note that when $[GLc]_{tot}>>Kd$ and $[GLc]_{tot}>>[Pro]_{tot}$, the above two equations may be simplified to the following form:

$$F=F_0+[(F_{const}*x)/(1+x/Kd)]$$

Where $F_{inf}=F_0+F_{const}*x$.

TABLE 2

Summary of GGBP-H6 NBD Mutations

| Identification | Solution ΔF (%)[1] | Kd (mM) | Dye/Prot |
|---|---|---|---|
| WILD TYPE | intrinsic | 0.0002 | |
| A1S, E149C, A213R, L238S | +21[2] | | 0.31 |
| A1S, E149C, A213S, L238S | +480 | 0.37 | 0.9 |
| K11C | 10 | | 1.8 |
| D14C | 1 | | 1.5 |
| V19C | −56 | 0.0001 | 0.38 |
| N43C | 40 | 0.0002 | 0.28 |
| G74C | −3 | 0.0009 | 1.43 |
| Y107C | −30 | 0.001 | 0.93 |
| T110C | −9 | | |
| S112C | 220 | 0.05 | 1.15 |
| S112C, L238S | 6 | | 1.5 |
| K113C | 15 | | 0.65 |
| K137C | −5 | <0.0002 | 1.17 |
| E149C | 300 | 0.0002 | 0.96 |
| E149C, A213C | 1400[4] | 0.1 | 2.2 |
| E149C, A213R | 660 | 1 | 1.1 |
| E149C, A213S | 240[4] | 0.0023 | 1.1 |
| E149C, A213T | 350 | 1 | 0.6 |
| E149C, A213L | 280 | 0.1 | 1.1 |
| E149C, A213Y | 280 | 0.1 | 1.1 |
| E149C, A213C, L238C | 180[2] | 8.5 | 2.8 |
| E149C, A213C, L238S | 900[2] | 11 | 1.7 |
| E149C, A213R, L238C | 430[2] | 11.1 | 1.6 |
| E149C, K223N | 260 | 0.003 | 0.7 |
| E149C, L238C | 260 | 5 | 1.6 |
| E149C, L238S | 660[3] | 0.08 | 1.36 |
| E149C, N256S | 1 | | 0.93 |
| E149C, N256R | 200 | >700 | 0.9 |
| E149C, M182C, A213C, L238S | 200 | >200 | 3.2 |
| E149C, A213S, L238S | 480 | 0.47 | 0.76 |
| E149C, A213R, L238S | 500 | 12 | 1.1 |
| H152C | 210 | 0.07 | 1.3 |
| H152C, A213S | 100 | 0.16 | |
| H152C, A213R | −3 | | 1.2 |
| H152C, K223N | 200 | 0.003 | 1 |
| M182C | 11 | | |
| A213C | 50 | 0.124 | 0.68 |
| A213C, L238C | 24, 67[2] | 6 | 1.4 |
| A213C, L255C | −5 | | 0.98 |
| M216C | 67 | 0.008 | 0.91 |
| D236C | +2[2] | | 0.43 |
| L238C | −6, +3[2] | 0.003[4] | 1.3 |
| D287C | 4 | | 1.1 |
| R292C | −34 | 0.0008 | 1.5 |
| V296C | −10 | <0.0002 | 1.08 |

[1] ΔF from 0 to 1 mM Glc
[2] ΔF when measured from 0 to 100 mM Glc
[3] ΔF when measured from 0 to 10 mM Glc
[4] Determined by SPR (Surface Plasmon Resonance)

Example 5

Figure 3:
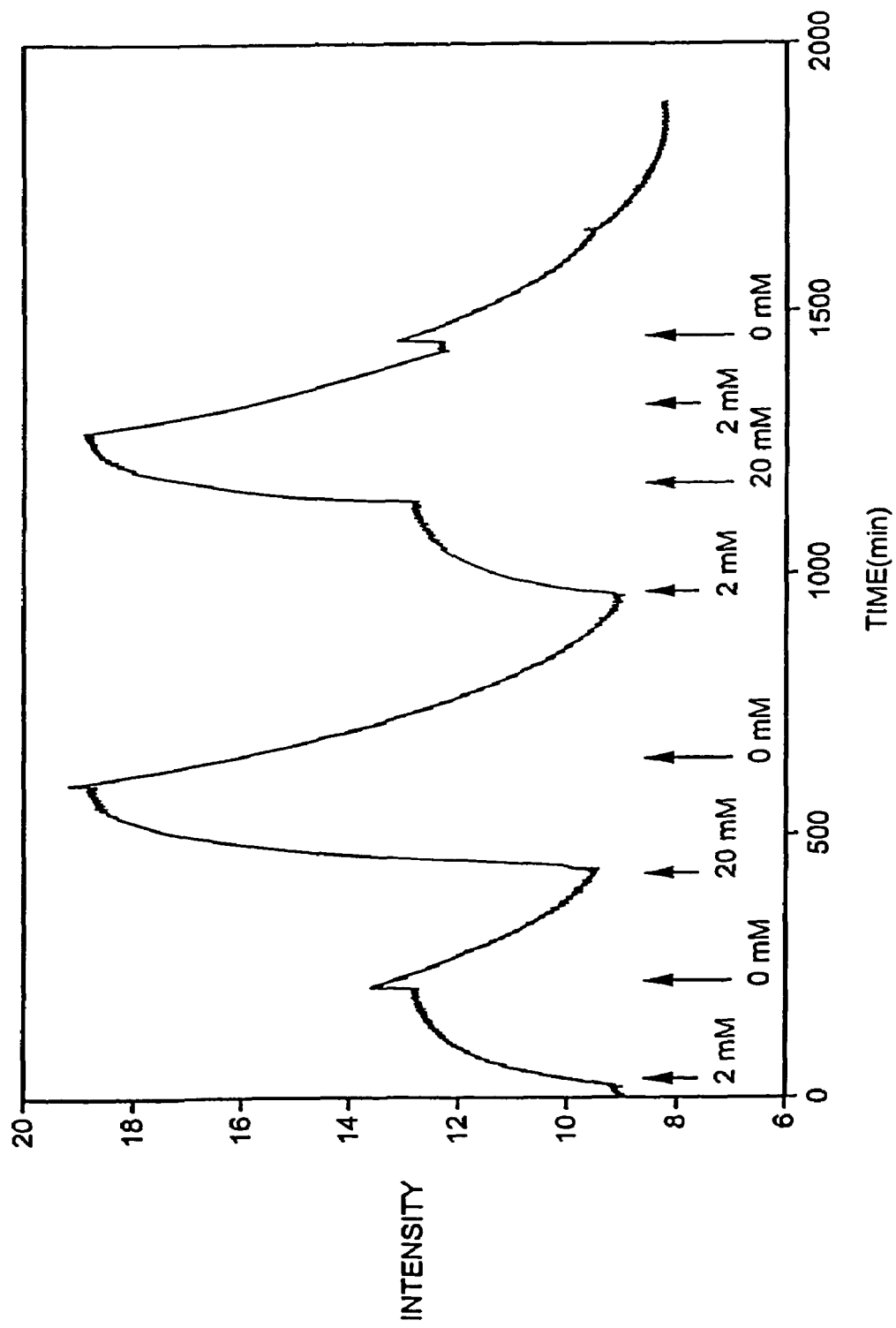
FIG. 3 illustrates reversible signal transduction from a mutated binding protein following exposure to solutions of glucose at the indicated concentrations.

Immobilization of a Biosensor of the Instant Invention into a Dialysis Membrane Matrix and the Ability of the Matrix to Provide Reversible and Continuous Readings Using a Varian Eclipse fluorimeter with a fiber optic attachment, GGBP L238C/A213C protein (2 M in PBS buffer) entrapped within a dialysis membrane having a molecular cut-off of 3500 Daltons affixed to the distal end of the fiber. Solutions were prepared containing PBS buffer, 2 mM, and 20 mM glucose in PBS buffer. With the probe in PBS solution, readings were recorded at 0.02 seconds intervals of the emission wavelength 521 nm, followed by insertion of the fiber into the glucose solutions. Replacement of the fiber into buffer-only solution resulted in the return of initial signal. FIG. 3 depicts multiple cycles alternating between buffer and glucose solutions demonstrating the reversibility of the biosensor entrapped within a permeable matrix within physiological range.

Example 6

The "CCS" Mutant (NBD Labeled E149C, A213C, L238S GGBP)

A particularly preferred embodiment of the invention is a triple mutant including a cysteine substituted for glutamic acid at position 149, a cysteine substituted for alanine at position 213 and a serine substituted for leucine at position 238 (E149C/A213C/L238S). Because this mutant has two cysteine sites, several combinations of molecules can be attached: one dye, two dyes, a dye and a quenching molecule, a dye and an attachment molecule (for immobilization). This mutant is particularly useful in the glucose protection scheme described in U.S. application Ser. No. 10/428,295 filed May 2, 2003, which is incorporated herein by reference. When E149C/A213C/L238S, also known as "CCS", is labeled with two NBD molecules, the $K_d$ is approximately millimolar and the ΔF can be 900%. In general, the higher the ΔF, the greater the dynamic range, and the higher the error tolerance of an instrument based on the protein.

FIG. 4 shows the change in fluorescence emission upon adding 100 mM glucose to a solution of CCS labeled with two NBD molecules.

CCS retains activity when immobilized onto alginate disks, as described in U.S. application Ser. No. 10/428,295, filed May 2, 2003, or alginate fibers, as described in the application entitled "Miniaturizable Fluorescence Biosensor" filed on Nov. 26, 2003, thereby demonstrating utility for use in detection devices and processes.

Example 7

The CCS Mutant (E149C, A213C, L238S) Labeled with NBD and Texas Red

The CCS protein has also been prepared with approximately 1 NBD dye/protein, and approximately the same amount of Texas Red dye/protein (NBD-TR-CCS). Except where noted, the procedure was performed at room temperature. 1 NBD-CCS was prepared using the general form of the ligand masking method described in U.S. application Ser. No. 10/428,295, filed May 2, 2003. GGBP protein (40 nmoles; 1.26 mg/mL) was diluted to 0.7 mg/mL using PBS buffer in a microcentrifuge tube, then five (5) molar equivalents of DTT per cysteine on the protein was added. After mixing for 15 minutes, 180 µL of 1M glucose in PBS was added (final concentration 82 mM) and the solution was mixed for another 30 minutes (ligand masking). The final concentration of glucose was chosen to saturate most of the glucose binding sites in the GGBP mutant. For the dye labeling, IANBD was added as a 0.5 mg/mL solution, in DMSO (20 µL) to the tube and the solution was mixed for 30 minutes in the dark. The dye-labeled protein was then separated from free dye by elution from a NAP-25 size exclusion column eluting with PBS buffer. Dialysis at 4° C. against PBS was used to remove any remaining free dye and glucose. The dye:protein ratio was determined by comparison of absorbance spectra of the eluted protein fractions, and found to be 1.

To prepare NBD-TR-CCS, one (1) NBD-CCS (0.5 mg/mL, 280 μL, 4 nmoles) was combined with 2 μL of 10 mM DTT for 15 minutes. Then, 3.3 μL of 12 mM Texas Red in DMSO was added to the solution and incubated for 5 hours. The free dye was removed with a NAP-5 size exclusion column and eluted with PBS buffer. The protein was filtered through a 100 kD filter to remove aggregates and was stored at 4° C. The presence of Texas Red on the protein was verified by examining the absorbance spectra of the protein. (Calculation of the exact dye/protein ratio for Texas Red was unclear due to the overlapping absorbance spectra of the Texas Red and NBD.)

FIG. 5 shows the change in fluorescence emission for a solution of NBD-TR-CCS upon addition of varying amounts of glucose. The excitation wavelength was 475 nm. The emission of NBD and Texas Red occur at 540 nm and 610 nm respectively. The ratio of emission at these two wavelengths can be used to determine glucose concentration providing a value that should be substantially independent of optical interference or fluctuations in excitation intensity. FIG. 6 is a plot of the emission ratio of NBD and Texas Red using the emission spectra from FIG. 5.

Example 8

The "CRC" Mutant (NBD-Labeled E149C,A213R,L238C GGBP)

A triple mutant including a cysteine substituted for glutamic acid at position 149, an arginine substituted for alanine at position 213 and a cysteine substituted for leucine at position 238 (E149C/A213R/L238C) was prepared and labeled with approximately two (1.6) NBD molecules per protein by a procedure similar to that of the CCS protein in Example 6. FIG. 7 shows the change in fluorescence emission upon adding 100 mM glucose to a solution of E1149C, A213R,L238C GGBP labeled with two NBD molecules.

We claim:

1. A composition comprising:
a mutated *E. coli* glucose/galactose binding protein having at least two amino acid substitutions in the amino acid sequence of SEQ ID NO:1, the at least two amino acid substitutions being selected from the group consisting of a cysteine at position 112 and a serine at position 238, a cysteine at position 149 and a serine at position 238, a cysteine at position 152 and a serine at position 213, a cysteine at position 213 and a cysteine at position 238, a cysteine at position 149 and an arginine at position 213, a cysteine at position 149 and a cysteine at position 213, a cysteine at position 149 and a threonine at position 213, a cysteine at position 149 and a leucine at position 213, a cysteine at position 149 and a tyrosine at position 213, a cysteine at position 149 and a serine at position 213, a cysteine at position 149 and an asparagine at position 223, a cysteine at position 149 and a cysteine at position 238, a cysteine at position 149 and a serine at position 256, a cysteine at position 149 and an arginine at position 256, a cysteine at position 152 and an arginine at position 213, a cysteine at position 152 and an asparagine at position 223, and a cysteine at position 213 and a cysteine at position 255.

2. The composition of claim 1 wherein said mutated glucose/galactose binding protein additionally comprises at least one histidine tag.

3. The composition of claim 1 wherein said mutated glucose/galactose binding protein additionally comprises at least one reporter group.

4. The composition of claim 3 wherein said reporter group is a luminescent label.

5. The composition of claim 4 wherein said luminescent label has an excitation wavelength of more than about 600 nanometers.

6. The composition of claim 4 wherein said luminescent label has an emission wavelength of more than about 600 nanometers.

7. The composition of claim 4 wherein said luminescent label is covalently coupled to said mutated glucose/galactose binding protein by reacting said mutated binding protein and at least one member selected from the group consisting of fluorescein, coumarins, rhodamines, 5-TMRIA (tetramethylrhodamine-5-iodoacetamide), (9-(2(or 4)-(N-(2-maleimdyl-ethyl)-sulfonamidyl)-4(or 2)-sulfophenyl)-2,3,6,7,12,13,16,17-octahydro-(1H,5H,11H,15H-xantheno(2,3,4-ij:5,6,7-i'j') diquinolizin-18-ium salt) (Texas Red®), 2-(5-(1-(6-(N-(2-maleimdylethyl)-amino)-6-oxohexyl)-1,3-dihydro-3,3-dimethyl-5-sulfo-2H-indol-2-ylidene)-1,3-propyldienyl)-1-ethyl-3,3-dimethyl-5-sulfo-3H-indolium salt (Cy™3), N-((2-iodoacetoxy)ethyl)-N-methyl)amino-7-nitrobenzoxadiazole (IANBD), 6-acryloyl-2-dimethylaminonaphthalene (acrylodan), pyrene, 6-amino-2,3-dihydro-2-(2-((iodoacetyl) amino)ethyl)-1,3-dioxo-1H-benz(de)isoquinoline-5,8-disulfonic acid salt (lucifer yellow), 2-(5-(1-(6-(N-(2-maleimdyl-ethyl)-amino)-6-oxohexyl)-1,3-dihydro-3,3-dimethyl-5-sulfo-2H-indol-2-ylidene)-1,3-pentadienyl)-1-ethyl-3,3-dimethyl-5-sulfo-3H-indolium salt (Cy™5), 4-(5-(4-dimethylaminophenyl)oxazol-2-yl)phenyl-N-(2-bromoacetamidoethyl)sulfonamide (Dapoxyl(2-bromoacetamidoethyl)sulfonamide)), (N-(4,4-difluoro-1,3,5,7-tetramethyl-4-bora-3a,4a-diaza-s-indacene-2-yl) iodoacetamide (BODIPY® 507/545 IA), N-(4,4-difluoro-5,7-diphenyl-4-bora-3a,4a-diaza-s-indacene-3-propionyl)-N'-iodoacetylethylenediamine (BODIPY 530/550 IA), S-((((2-iodoacetyl)amino)ethyl)amino)naphthalene-1-sulfonic acid (1,5-IALDANS), and carboxy-X-rhodamine, 5/6-iodoacetamide (XRIA 5,6).

8. The composition of claim 1, wherein said mutated glucose/galactose binding protein additionally comprises two luminescent reporter groups covalently coupled to said binding protein.

9. The composition of claim 8, wherein said two luminescent reporter groups are both N-((2-iodoacetoxy)ethyl)-N-methyl)amino-7-nitrobenzoxadiazole (IANBD), or wherein one of said luminescent reporter groups is N-((2-iodoacetoxy)ethyl)-N-methyl)amino-7-nitrobenzoxadiazole (IANBD) and the other said luminescent reporter group is (9-(2(or 4)-(N-(2-maleimdylethyl)-sulfonamidyl)-4(or 2)-sulfophenyl)-2,3,6,7,12,13,16,17-octahydro-(1H,5H,11H,15H-xantheno(2,3,4-ij:5,6,7-i'j')diquinolizin-18-ium salt) (Texas Red®).

* * * * *

SEQUENCE LISTING

<160> NUMBER OF SEQ ID NOS: 1

<210> SEQ ID NO 1
<211> LENGTH: 309
<212> TYPE: PRT
<213> ORGANISM: Escherichia coli

<400> SEQUENCE: 1

```
Ala Asp Thr Arg Ile Gly Val Thr Ile Tyr Lys Tyr Asp Asp Asn Phe
1               5                   10                  15

Met Ser Val Val Arg Lys Ala Ile Glu Gln Asp Ala Lys Ala Ala Pro
            20                  25                  30

Asp Val Gln Leu Leu Met Asn Asp Ser Gln Asn Asp Gln Ser Lys Gln
        35                  40                  45

Asn Asp Gln Ile Asp Val Leu Leu Ala Lys Gly Val Lys Ala Leu Ala
    50                  55                  60

Ile Asn Leu Val Asp Pro Ala Ala Ala Gly Thr Val Ile Glu Lys Ala
65                  70                  75                  80

Arg Gly Gln Asn Val Pro Val Val Phe Phe Asn Lys Glu Pro Ser Arg
                85                  90                  95

Lys Ala Leu Asp Ser Tyr Asp Lys Ala Tyr Tyr Val Gly Thr Asp Ser
            100                 105                 110

Lys Glu Ser Gly Ile Ile Gln Gly Asp Leu Ile Ala Lys His Trp Ala
        115                 120                 125

Ala Asn Gln Gly Trp Asp Leu Asn Lys Asp Gly Gln Ile Gln Phe Val
    130                 135                 140

Leu Leu Lys Gly Glu Pro Gly His Pro Asp Ala Glu Ala Arg Thr Thr
145                 150                 155                 160

Tyr Val Ile Lys Glu Leu Asn Asp Lys Gly Ile Lys Thr Glu Gln Leu
                165                 170                 175

Gln Leu Asp Thr Ala Met Trp Asp Thr Ala Gln Ala Lys Asp Lys Met
            180                 185                 190

Asp Ala Trp Leu Ser Gly Pro Asn Ala Asn Lys Ile Glu Val Val Ile
        195                 200                 205

Ala Asn Asn Asp Ala Met Ala Met Gly Ala Val Glu Ala Leu Lys Ala
    210                 215                 220

His Asn Lys Ser Ser Ile Pro Val Phe Gly Val Asp Ala Leu Pro Glu
```

-continued

```
            225                 230                 235                 240
Ala Leu Ala Leu Val Lys Ser Gly Ala Leu Ala Gly Thr Val Leu Asn
                    245                 250                 255

Asp Ala Asn Asn Gln Ala Lys Ala Thr Phe Asp Leu Ala Lys Asn Leu
                260                 265                 270

Ala Asp Gly Lys Gly Ala Ala Asp Gly Thr Asn Trp Lys Ile Asp Asn
            275                 280                 285

Lys Val Val Arg Val Pro Tyr Val Gly Val Asp Lys Asp Asn Leu Ala
        290                 295                 300

Glu Phe Ser Lys Lys
305
```